United States Patent [19]

Chiusoli et al.

[11] Patent Number: 4,468,522
[45] Date of Patent: Aug. 28, 1984

[54] PROCESS FOR THE PREPARATION OF (OMEGA-CARBOALKOXY-NOR.ALKYL)-DIALKYLAMINES

[75] Inventors: Gian Paolo Chiusoli, Parma; Mirco Costa, Reggio Emilia; Luciano Pallini, Fornovo Taro; Giuliana Terenghi, Castelnovo di Sotto, all of Italy

[73] Assignee: Anic S.p.A., Palermo, Italy

[21] Appl. No.: 366,095

[22] Filed: Apr. 6, 1982

[30] Foreign Application Priority Data

Apr. 10, 1981 [IT]  Italy ................................ 21030 A/81

[51] Int. Cl.$^3$ ............................................ C07L 101/18
[52] U.S. Cl. ....................................... 560/155; 544/171
[58] Field of Search ........................... 560/155; 544/171

[56] References Cited

FOREIGN PATENT DOCUMENTS 682160 11/1952 United Kingdom .

*Primary Examiner*—Michael L. Shippen
*Attorney, Agent, or Firm*—Morgan, Finnegan, Pine, Foley & Lee

[57] ABSTRACT

Process for the preparation of (omega-carbalkoxy-nor.alkyl) dialkylamines having a linear alkyl chain, comprising the steps of amination of allyl compounds in which at least an allyl carbon atom is a part of a cyclopropane ring which contains one or two carboxyl or carbalkoxy groups on the carbon atom which is adjacent to the allyl carbon, or is a part of a lactone ring, in the presence of catalysts consisting of triarylphosphine complexes of palladium, or trialkyl phosphite complexes of nickel, and the subsequent hydrogenation of the unsaturated amine thus obtained. By so doing, interesting linear amines are obtained, which contain carboxyl units or carbalkoxy units, said amines being useful as additives for the industry of synthetic fibres (viscosity stabilizers for polycaprolactam).

8 Claims, No Drawings

PROCESS FOR THE PREPARATION OF (OMEGA-CARBOALKOXY-NOR.ALKYL)-DIALKYLAMINES

This invention relates to a process for the production of (omega-carbalkoxy-nor.alkyl) dialkylamines having a substantially straight linear alkyl chain, which are useful as additives for the industries of the synthetic fibres, for example as viscosity stabilizers for polycaprolactam.

Studies are under way long since on the amination reactions of alkyl compounds. By such studies it has been possible to prepare, as a rule, amines starting from olefin compounds which contain functional groups, wherein the functional group is substituted by the amine function.

Such reactions are favourably catalyzed, so that they can be carried out under bland conditions, by complexes of palladium and nickel.

According to the known art (see for example: Akemark and Zetterberg, Tetrahedron Letters, 3733 (1975); Atkins, Walter and Manyk, Tetrahedron Letters, 3821 (1970); Trost and Keinan, J. Org. Chem. 44, 3451 (1979); Furukawa, Kiji, Yamamoto and Tokyo, Tetrahedron, 29 3149 (1973), the amination of allyl compounds, catalyzed by palladium, produces, besides the straight-line product, considerable amounts of the product resulting from the attachment to the internal allyl carbon atom.

It has now been found, and this is the subject matter of the present invention, that olefin compounds, the allyl carbon atom of which belongs to a cyclopropane ring which contains one or two carboxyl or carbalkoxy groups on the carbon atom adjacent to the allyl carbon atom, or which is a part of a lactone ring, may, when placed in the presence of specific complexes of palladium or nickel, selectively add dialkylamines to the end carbon atom of the olefin, with a concurrent cleavage of the cyclopropane or lactone ring, thus originating straight-line amine derivatives.

This kind of addition is still more unpredictable, in that, when no catalyst is present, the amination, upon the cleavage of the cyclopropane ring, takes place integrally on the internal allyl carbon atom, that is, on the atom which is adjacent to the unsaturated carbon atom which has been originated by the ring cleavage, so that a branched-structure product is only originated. (see: S. Danishefsky, Acc. Chem. Res., 12, 66 (1979).

According to the present invention, as defined in the claims, a process is provided, for the preparation of (omega-carbalkoxyalkyl)-dialkylamines having a substantially straight-line alkyl chain, said process being characterized by comprising the steps of selectively attaching dialkylamines to the end position of an allyl system or of a system which is a part, with its internal carbon atom, of a cyclopropane ring containing one or two carboxyl or carbalkoxy groups on the carbon atom adjacent to the allyl carbon atom, or of a system being a part of a lactone ring, or completely inserted into a lactone ring.

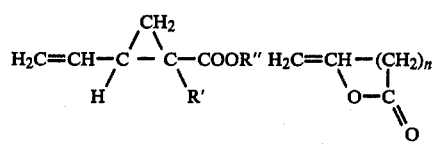

-continued

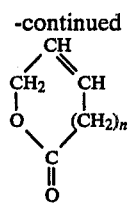

wherein R' is either H or COOR", R" is H or an alkyl radical containing from 1 to 4 carbon atoms, and n is an integer from 1 to 3, in the presence of catalysts consisting of triarylphosphine complexes of palladium, or trialkylphosphite complexes of nickel, and subsequently hydrogenating the thus obtained unsaturated amine.

More particularly, the amination of the substrates to be used in the present invention, namely 1,1-disubstituted vinylcyclopropane, gamma-vinylbutyro-lactone and the lactone of the 6-hydroxy-4-hexenoic acid, is entirely targeted at the terminal allyl carbon atom, by using, as catalysts, triarylphosphine complexes of palladium or trialkylphosphite complexes of nickel, more particularly tris- or tetrakis-(triphenylphosphine)-palladium, and tris- or tetrakis-(triisopropylphosphite)-nickel.

The reaction takes place favourably in solution; the solvent can be composed of the reagents themselves, or of ethereal or esteric solvents, having, if possible, a boiling point temperature below 150° C. (this for questions of cheapness in the separation of the solvents, if any, from the end products). The catalytic complexes used herein permits to achieve high values of catalytic efficiency, inasmuch as it is permissible to use dialkylamine-to-catalyst ratios up to 50,000 and over.

Even without totally optimizing the process, values have been attained, in the case of palladium complexes, as high as 4,000 converted molecules per molecule of catalytic complex, and, in the case of nickel complexes, values of 15 molecules per molecule of nickel complex. The ratio of the dialkylamine to the olefin substrate may be varied from 1 to 3, the extreme values included.

It has thus been made possible to arrive at the addition of dialkylamines, in which the alkyl group contained up to 20 carbon atoms, to cyclopropane compounds of the type:

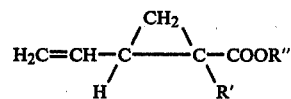

wherein R' is H or COOR", and R" is H or an alkyl containing from 1 to 4 carbon atoms, and also to gamma-vinylbutyrolactone and to the lactone of the 6-hydroxy-4-hexenoic acid.

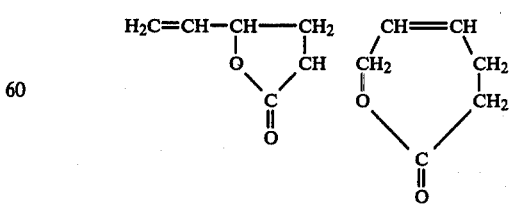

to a virtually total extent on the external carbon atom of the allyl group, while then obtaining, by subsequent hydrogenation, interesting straight-line amines which contain carboxyl or carbalkoxy groups, which are useful as additives, for the synthetic fibre industry, as viscosity stabilizers for polycaprolactam, for example.

By way of illustration only, a few examples of amination reactions, carried out according to the process of this invention are reported hereunder.

EXAMPLE 1

A 25-ml flask is charged, in a nitrogen atmosphere, with 0.020 g of Pd(PPh$_3$)$_4$. Then, 7 mls of anhydrous and de-aerated tetrahydrofuran are added and, thereafter, 1.94 g of gamma-vinylbutyrolactone and 2.15 g of diethylamine. A yellow homogeneous solution is now formed, which, by means of an oil bath, is maintained at 80° C. for 20 hours. The mixture is allowed to cool and both the excess tetrahydrofuran and diethylamine are removed by evacuation. The oily residue is supplemented with 10 mls of anh.methanol and gaseous hydrogen chloride is bubbled for about two hours through the solution. The solution is evaporated to dryness and the residue is taken up with water, where on the acidic solution is extracted with ethyl ether. The aqueous solution, made alkaline with sodium carbonate, is extracted with ethyl ether once again. The ethereal extract essentially contains the compound (5-carbomethoxy)-2-pentenyldiethylamine.

By hydrogenation in methanol with Ni-Raney as the catalyst, there are obtained 2.61 g of (5-carbomethoxy-nor.pentyl)-diethylamine, which correspond to a yield of 75% relative to the lactone fed to the reaction, and to a catalytic efficiency of 750 mols of product per mol of palladium complex.

Starting from 2.67 g of vinylbutyrolactone, 3.0 g of diethylamine and 0.0065 g of Pd(PPh$_3$)$_4$ in 5 mls of tetrahydrofuran, there are obtained 3.28 g (0.01633 mol) of end product, (69%, 2916 mols per mol of Pd complex).

Reactions of this kind can be carried out in ethyl acetate or anisole.

Similar results are obtained by using, instead of diethylamine, diisopropylamine, morpholine and dodecylmethylamine.

EXAMPLE 2

Under the same conditions as in Example 1, a reaction is carried out with 0.008 g of Pd(PPh$_3$)$_4$ in 7 mls of acetonitrile and 0.780 g of gamma-vinylbutyrolactone, with 0.85 g of diethylamine. By heating to 80° C., there is obtained, after a short time, a homogeneous solution, which is maintained at that temperature (80° C.) for 20 hours. By operating as in Example 1, there is obtained 1.1 g of (5-carbomethoxy-nor.pentyl) diethylamine, which corresponds to a yield of 79% relative to the employed lactone, and to a catalytic efficiency of 799 mols of product per mol of palladium complex.

EXAMPLE 3

Under the same conditions as in Example 1, there are reacted 0.076 g of Ni [P(OisoPr)$_3$]$_4$ in 10 mls of acetonitrile with 0.30 g of gamma-vinylbutyrolactone and 0.87 g of diethylamine. The reaction mixture is heated to 110° C. for 40 hours. By operating as in Example 1, there are obtained 0.13 g of (5-carbomethoxy-nor.pentyl) diethylamine, corresponding to a yield of 24% relative to the lactone employed, and to a catalytic efficiency of 8 mols of product per mol of nickel complex.

EXAMPLE 4

Under the same conditions as in Example 1, there are reacted without using any solvent 0.052 g of Pd(PPh$_3$)$_4$ 0.91 g of gamma-vinylbutyrolactone and 1.18 g of diethylamine. There are obtained 0.92 g of final hydrogenation product, which corresponds to a yield of 56% relative to the lactone used, and to a catalyst efficiency of 101 mols of product per mol of catalytic complex.

EXAMPLE 5

Under the conditions of Example 4 the lactone of the 6-hydroxy-4-hexenoic acid, which has been prepared together with the vinylbutyrolactone in the ratio of about 1:1 by treating the vinylcyclopropanedicarboxylic ester at 160° C. (bath temperature) under a vacuum of about 1 mm of mercury, and separated by chromatography on silica-gel, is reacted, in an amount of 0.715 g with 0.012 g of Pd(PPh$_3$)$_4$, 0.0790 g of Et$_2$NH, and 5 mls of tetrahydrofuran for 17 hours at 80° C.

Upon like treatments, the same final hydrogenated product is obtained (0.858 g, i.e. 415 mols per mol of catalyst).

EXAMPLE 6

Under the same conditions of Example 1, there are reacted 0.013 g of Pd(PPh$_3$)$_4$ with 0.84 g of 1,1-dicarboethoxy-2-vinylcyclopropane and 0.860 g of diethylamine.

After 24 hours at room temperature, the reaction mixture is distilled under vacuum and there is obtained 1.1 g of (5,5-dicarboethoxy-2-pentenyl) diethylamine, corresponding to an analytical yield of about 100% and to a catalytic efficiency of 343 mols of product per mol of palladium complex. Upon addition, after the first 24 hours, of 0.717 g of dicarboethoxyvinylcyclopropane 224 additional mols are converted per mol of Pd-complex.

The hydrogenation in ethanol in the presence of Ni-Raney, followed by decarboxylation on acetic acid: sulphuric acid (95% conc.): water in the proportion of 1:1:1 and the subsequent esterification with ethanol and gaseous HCl produce 1.24 g of (5-carbomethoxypentyl) diethylamine, corresponding to a yield of 94% relative to the cyclopropane which has been used.

EXAMPLE 7

Under the same conditions as in Example 5 there are used 0.005 g of Pd(PPh$_3$)$_4$ in 3 mls of tetrahydrofuran, 0.63 g of 1,1-dicarboethoxy-2-vinylcyclopropane and 0.56 g of diethylamine. By operating as in Example 5, there is obtained 0.395 g of (5-carbomethoxy-nor.pentyl)diethylamine, corresponding to a yield of 66% relative to the cyclopropane which has been used and to a catalytic efficiency of 446 mols of product per mol of palladium complex. In addition, there is recovered 0.20 g of the unreacted cyclopropane, corresponding to the 32% of that which had been introduced originally.

The catalytic efficiency is in the order of magnitude of 4,000 mols per mol of Pd-complex and can be attained after several days at room temperature.

EXAMPLE 8

Under the same conditions as in Example 5, there are reacted 0.011 g of Pd(PPh$_3$)$_4$ in 2.3 mls of acetonitrile with 0.52 g of 1,1-dicarboethoxy-2-vinylcyclopropane and 0.53 g of diethylamine.

By operating as in Example 5 there is obtained 0.41 g of (5-carbomethoxy-nor.pentyl) diethylamine, which corresponds to a yield of 83% on the originally fed cyclopropane and to a catalytic efficiency of 210 mols per mol of palladium complex. Similar results can be obtained when operating with 1,1-dicarboxy-2-vinylcyclopropane in lieu of the corresponding diester.

Instead of acetonitrile, there can be used, with similar results, ethyl acetate and anisole.

EXAMPLE 9

There are reacted 0.038 g of Ni [P(OsioPr)$_3$]$_4$ in 4 mls of tetrahydrofuran with 0.455 g of 1,1-dicarboethoxy-2-vinylcyclopropane and 0.46 g of diethylamine at 80° C. for 24 hours.

Operating as in the previous Examples, there is obtained 0.12 g of (5-carbomethoxypentyl) diethylamine with a yield of 20% and a catalytic efficiency of 15 mols per mole of catalytic complex.

There is recovered 0.36 g (80%) of the starting cyclopropane.

We claim:

1. A process for preparing (5-carbomethoxy-n-pentyl)-diethylamine comprising the steps of:
   (a) mixing and reacting diethylamine and gamma-vinylbutyrolactone in the presence of a catalyst selected from the group comprising triarylphosphine complexes of palladium and trialkylphosphite complexes of nickel;
   (b) treating the reaction product with methanol and hydrochloric acid to produce (5-carbomethoxy)-2-pentenyl-diethylamine; and
   (c) hydrogenating (5-carbomethoxy)-2-pentenyldiethylamine in the presence of Ni-Raney as a catalyst to form (5-carbomethoxy-n-pentyl)-diethylamine.

2. Process according to claim 1, characterized in that the triarylphosphine complex of palladium is selected from among tris- or tetrakis-(triphenylphosphine) palladium.

3. Process according to claim 1, characterized in that the trialkylphosphite complex of nickel is selected from among tris- or tetrakis (triisopropylphosphite) nickel.

4. A process according to claim 1 wherein the reaction of diethylamine and gamma-vinylbutyrolactone is carried out in a solvent selected from the group comprising ethers and esters.

5. A process according to claim 4 wherein the solvent is acetonitrile.

6. A process according to claim 4 wherein the solvent is tetrahydrofuran.

7. A process according to claim 1 wherein the reaction of diethylamine and gamma-vinylbutyrolactone is carried out at a temperature in the range of about 70° C. to about 110° C. for a period of time from about 20 hours to about 40 hours.

8. A process according to claim 1 wherein the molar reaction of diethylamine to gamma-vinylbutyrolactone is from about 10:1 to about 3:1.

* * * * *